United States Patent [19]

Love

[11] Patent Number: 5,405,405
[45] Date of Patent: Apr. 11, 1995

[54] PROSTHETIC SOCKET CONTAINING INFLATABLE MEANS

[76] Inventor: Michael G. Love, 6280 Walkers Corners Rd., South Byron, N.Y. 14557

[21] Appl. No.: 65,808

[22] Filed: May 21, 1993

[51] Int. Cl.⁶ .............................................. A61F 2/80
[52] U.S. Cl. ..................................... 623/37; 623/901; 264/222
[58] Field of Search .................................. 623/33–37, 623/901; 264/222, DIG. 30

[56] References Cited

U.S. PATENT DOCUMENTS

| | | |
|---|---|---|
| 1,868,303 | 7/1932 | Balch et al. |
| 1,893,853 | 1/1933 | Tullis |
| 2,634,424 | 4/1953 | O'Gorman |
| 3,671,980 | 6/1972 | Baird |
| 3,889,301 | 6/1975 | Bonner, Sr. |
| 4,300,245 | 11/1981 | Saunders |
| 4,432,101 | 2/1984 | Johnson |
| 4,655,779 | 4/1987 | Janowiak |
| 4,923,475 | 5/1990 | Gosthnian et al. ............ 623/37 |
| 5,108,456 | 4/1992 | Coonan, III .................... 623/37 |
| 5,133,776 | 7/1992 | Crowder ......................... 623/37 |
| 5,246,464 | 9/1993 | Sabolich ......................... 623/33 |

OTHER PUBLICATIONS

PNEU-FIT Brochure and Advertisement (4 pages).

*Primary Examiner*—David H. Willse
*Attorney, Agent, or Firm*—Harris Beach & Wilcox

[57] ABSTRACT

A composite socket member for use with a prosthetic appliance for a residual limb which comprises an outer socket which defines an inner cavity generally conforming to the outer surface of a residual limb, an inner socket which defines an inner cavity and being adapted to receive the residual limb, with the inner socket conforming to the shape of the outer socket and when nested within the cavity of the outer socket defines an air space between the inner surface of the outer socket and the outer surface of the inner socket and an inflatable bladder being disposed between the inner surface of the outer socket and the outer surface of the inner socket. The inner socket contains at least one opening through its side wall at a preselected weight-bearing location whereby upon inflation of the bladder, pressure is applied by the bladder through the side wall opening against the preselected weight-bearing location of the residual limb to control the movement and rotation stability of the prosthetic appliance. A method for making the composite socket member is also disclosed.

7 Claims, 3 Drawing Sheets

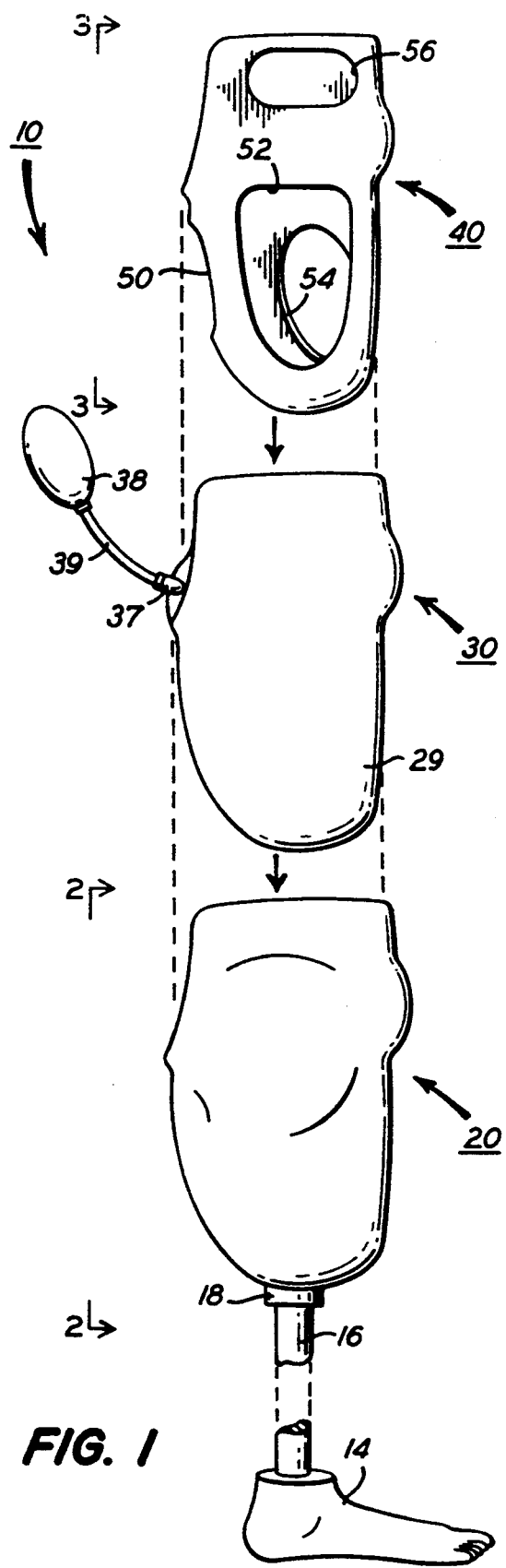
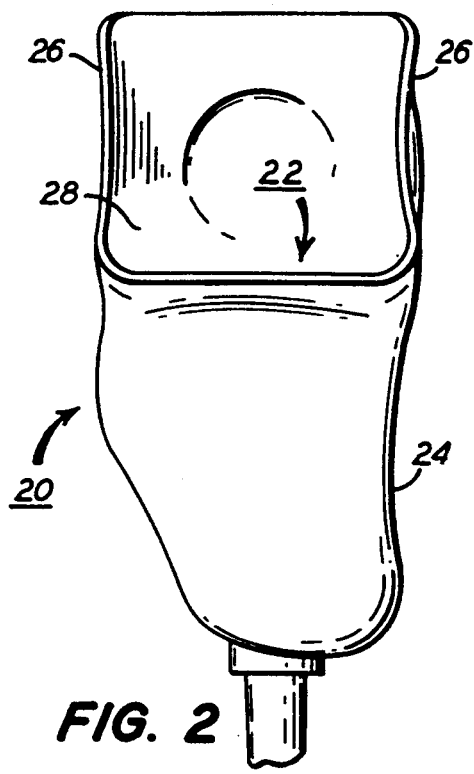
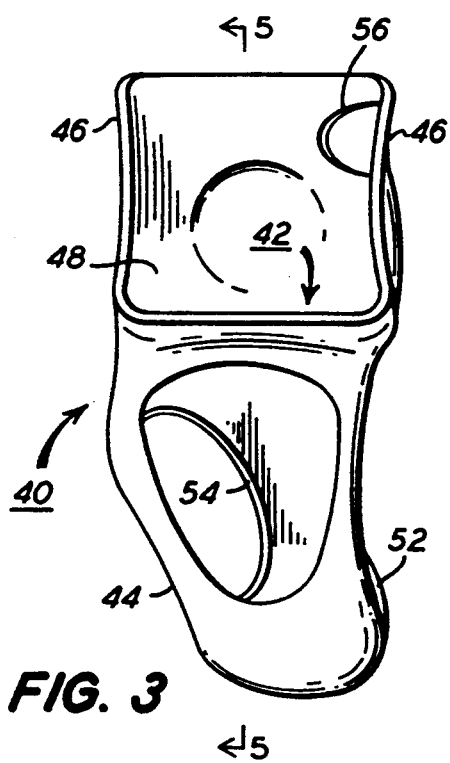
FIG. 1
FIG. 2
FIG. 3

PROSTHETIC SOCKET CONTAINING INFLATABLE MEANS

BACKGROUND OF THE INVENTION

The present invention relates in general to a prosthesis and more specifically to a composite socket which contains inflatable means.

Artificial limbs are usually provided with a socket into which the stump of a residual member is inserted. In the case of the below-knee amputee, for example, the function of the socket is to provide a weight bearing surface for the stump. The socket also functions to supply lateral support to the stump to maintain stability for the wearer, and is usually attached to an artificial limb that consists of a shin and ankle/foot section that completes the limb.

One of the most common problems amputees face on a daily basis is adjusting the fit of the socket to their ongoing needs. It is recognized that there is often a change in the volume of residual limb which may be slightly perceptible or significant depending on the situation. These volume changes cannot be completely accounted for or anticipated when making the socket because to a certain extent the human body is partially made of fluids. A majority of amputees have been the victims of diseases that effect the vascular system such as diabetes, and this vascular disease accounts for more amputations than any other single cause. The wearing of a prosthesis, with comfort, for members of this group can be especially difficult. The fluid volume within the body is dynamic, and can change in amounts as the person ages, but it also changes on a day-to-day basis.

The standard way for an amputee to adjust the fit of their below-knee socket is by wearing a stump sock(s). These socks are made from a variety of materials such as wool and cotton. The socks come in various thicknesses from one ply to eight plys of thickness of material. When the amputee feels the need, he may add or remove socks of various plys to adjust the fit of his socket. One difficulty associated with this technique is that the sock fits over the entire residual limb. Therefore, increasing the thickness of the plys can also increase the pressures over areas of the residual limb where it is not wanted. This can result in an increase of pressure over boney prominences of the below-knee residual limb.

It can therefore be seen that while adding and subtracting stump socks can solve some wearing problems, it can also create additional problems. Furthermore, this approach creates other problems for the prosthetic user, because it is often difficult to add or subtract stump socks when the need may arise. Obviously, this requires a private environment, and an individual must remove the prosthesis and add or remove stump socks and put the artificial limb back on. Access to privacy is unavailable much of the time during the day for some people, and carrying a supply of various prosthetic socks is also cumbersome and inconvenient.

There has, therefore, been a continual and long felt need for an adjustable system that does not rely on stump socks or visits to the prosthetist for adjustments to compensate for fitting problems.

One approach that has been seen in the field and described in certain patent literature utilizes an air system, with the principle of using air as an interface between the residual limb and the socket in an attempt to increase the comfort of ambulating with an artificial limb. However, for the amputee to simply put on an air sock and pump it up with air and expect it to be usable is an unreaslistic expectation. One reason why this simple broad approach to date has been unworkable is that it does not provide for rotational stability which is a must if the amputee is to control his prosthesis. It is essential, with this type of approach that the socket must have a contoured interface that closely matches the contours of the amputation, if stability is to take place. Nothing can replace the expertise of the prosthetist in determining where the best placement for file weight bearing areas will be on a wide variety of below-knee amputees.

Others in the field have suggested an inflatable pad or bladder, which allows the amputee to put an air pad into the socket and inflate it with air pressure. This system, however, is wanting in that there is only a small area to be effected by the air pad. Inflating the pad could cause too much pressure on the opposite side of the residual limb where the pad is not worn, since inflating the pad means squeezing the residual limb to the other side of the socket.

In the system of the present invention., an air bladder is used in which it becomes part of an integrated prosthetic socket designed by the prosthetist. The weight bearing areas are determined by the prosthetist by forming selected openings or holes through the inner socket wall, with the location of the openings as well as the size being made by the prosthetist to suit the needs of the amputee. This as will be shown allows the amputee to inflate or deflate the bladder and adjust the fit to their individual needs. Thousands of prosthetic devices are replaced each year because they no longer can be adjusted as to fit. It will be seen that the socket system of the present invention allows the amputee to adjust the socket for personal comfort in order to provide the proper pressure and the proper weight bearing locations against the residual stump to control the movement and rotational stability of the prosthetic appliance.

SUMMARY OF THE INVENTION

The present invention is directed to a composite or laminated stump receiving socket for a prosthesis device which preferably provides for improved control of movement and rotational stability of a below-knee prosthetic device. The composite socket comprises an outer molded plastic socket having an outer shell which defines an inner cavity generally conforming to the outer surface of a residual limb. An inner socket conforming to the shape of the outer socket and being sized and adapted to receive the residual limb is formed to be nested within the cavity of the outer socket, and is also sized to define an air space between the inner surface of the outer socket and the outer surface of the inner socket. A unitized inflatable bladder is disposed in the space between the inner surface of the outer socket and the outer surface of the inner socket with the bladder containing independently controlled inflation means. Preferably, the bladder is inflated by air, but other inflation means could be used with fluids other than air. The inner socket further contains a plurality of openings through its side walls at preselected weight bearing locations where upon inflation of the bladder, pressure is applied by the bladder through the side wall openings against the preselected weight bearing locations on the residual limb to control the movement and rotational stability of the prosthetic appliance.

The double walled composite structure of the socket of the present invention allows the prosthetist to determine where the eventual primary weight bearing areas will be placed. In the apparatus and system of the present invention, the air bladder becomes an integrated part of the prosthetic socket designed by the prosthetist, with the weight bearing areas determined by the prosthetist by selecting and forming openings in the inner socket. Both the shape of the areas of the openings, and their location, as well as heir size, are determined by the prosthetist on an individual basis depending upon the need. This allows the amputee to inflate or deflate the bladder and adjust the fit to their individual needs.

The specific nature of this invention as well as other objects and advantages thereof will become apparent from the consideration of the following specification and the following drawings.

BRIEF DESCRIPTION OF THE DRAWINGS

FIG. 1 is an exploded view of the composite socket of the present invention;

FIG. 2 is a rear view of the outer socket illustrated in FIG. 1;

FIG. 3 is a rear view of the inner socket illustrated in FIG. 1;

DETAILED DESCRIPTION OF THE INVENTION

Figure 4:
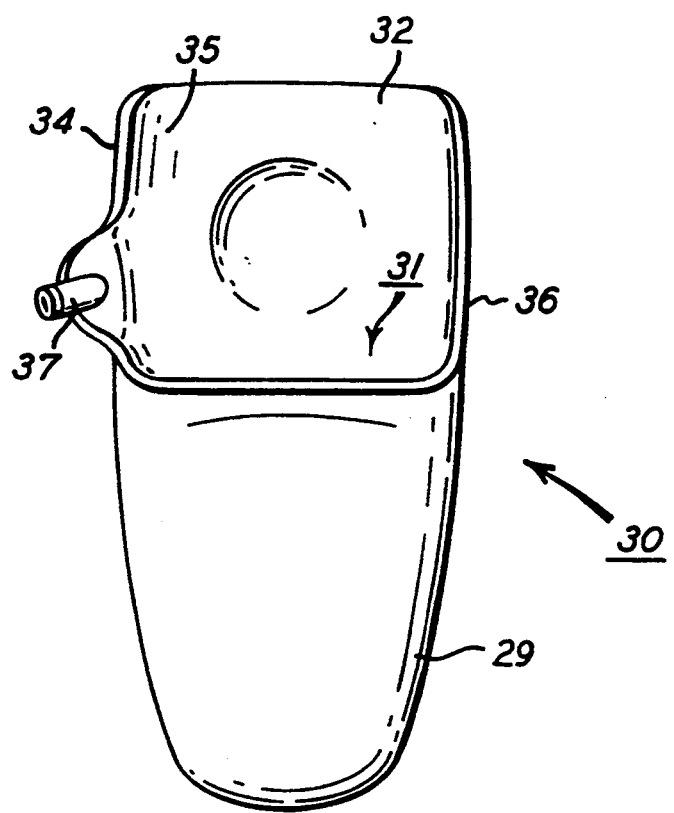
FIG. 4 is a rear view of the bladder illustrated in FIG. 1.

Referring to the drawings there is shown in FIG. 1 an artificial leg or prosthesis 10 of a type suitable to be worn by a below the knee amputee. It should be understood, however, that the preferred embodiment of the invention illustrated herein as a prosthetic device to be worn as an artificial leg by a below the knee amputee, has equal application to other types of artificial limbs such as the above knee prosthesis and similar or like prosthetic devices.

The leg 10 contains a composite socket 12 to which is affixed to a foot component 14 by endoskeletal pylon/ankle tube 16 through endoskeletal socket adaptor 18.

The composite socket 12 comprises an outer socket 20 and air chamber or bladder 30 disposed and nested therein, and an inner socket 40 nesting within the outer socket with the bladder 30 disposed between the walls of the outer and inner sockets.

Figure 5:
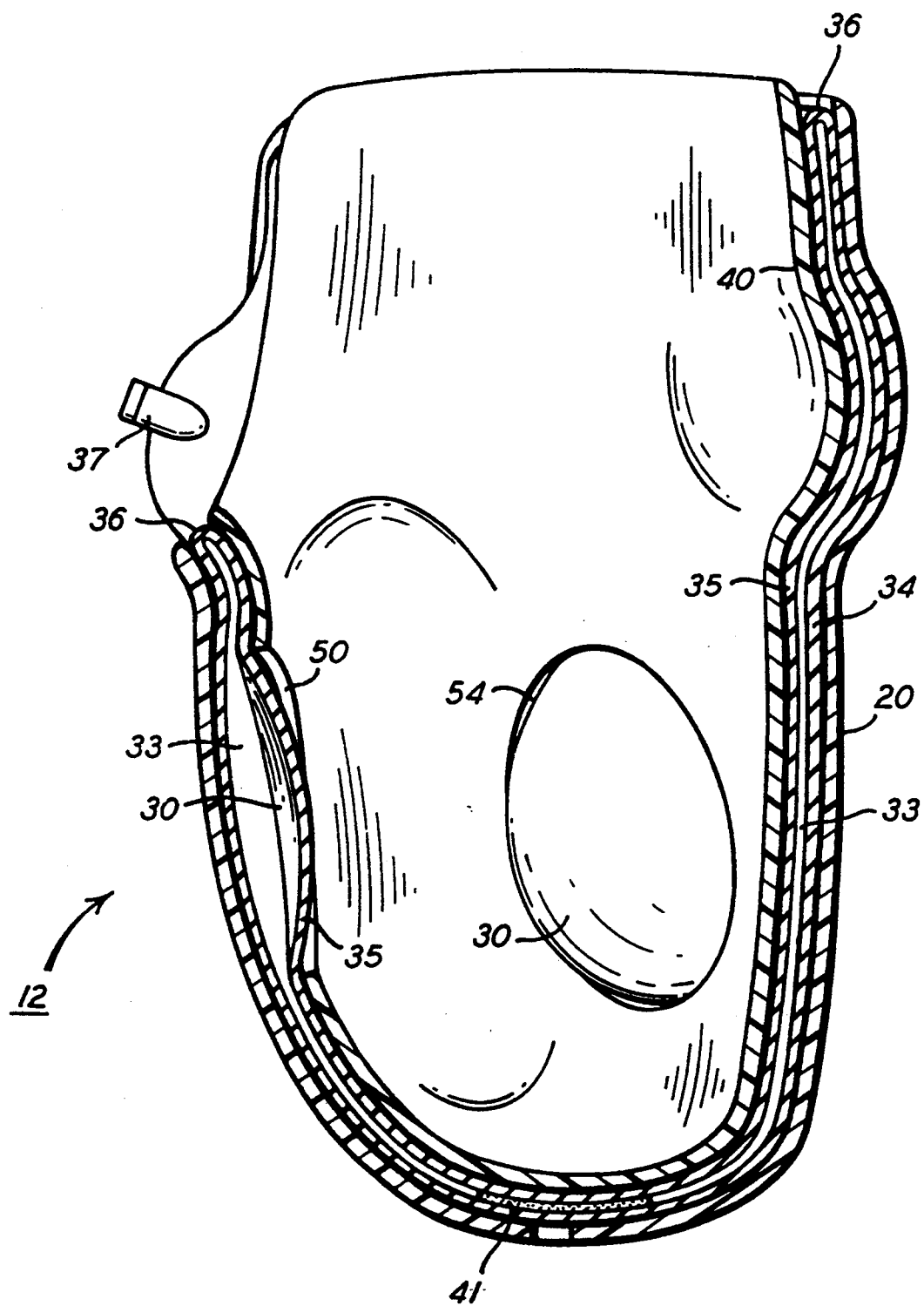
FIG. 5 illustrates an enlarged sectional view of composite socket along line 5—5 of FIG. 3 when the three components of the composite socket of FIG. 1 are in place nested within each other.

Outer socket 20 may comprise any suitable rigid or semi-rigid material such as polyester, acrylic, carbon fibre, fibre glass, plastics and the like. The socket may be formed by any conventional technique to be hereinafter described in greater detail. The internal cavity 22 of socket 20 is molded to assume the general configuration of the residual limb to be supported, and generally is cupped shaped in its lower section 24 with a pair of opposed ears 26 extending upwardly therefrom. The interior surface 28 of the outer socket is adapted to receive and contain a pneumatic or fluid bladder 30 which is formed of a soft pliable material such as a vinyl, rubber, polyurethane or the like which forms a double walled membrane 34 and 35 which is bonded to itself along outer bonding surfaces 36 to form a unitized inflatable bladder defining an internal air space, 33 illustrated more clearly in FIG. 5. The bladder contains an inner cavity 31 having an inner surface 32 and an outer surface 29 and is adapted to be independently controlled and inflated by the user through an air pump bulb 38 connected to air pump hose 39 which is directly connected to the sidewall of the bladder 30 at any convenient location by connector valve 37. In the embodiment illustrated in FIG. 5, the bladder is sealed at area 41 located at a portion of the bottom section to allow for total contact of the inner socket and the stump.

Bladder materials, configurations and specifications and their inflation systems which are available to the art which would be suitable for use in the present invention are disclosed in U.S. Pat. Nos. 4,300,245; 4,432,101; 4,923,475; 5,108,456 and 5,133,776 which are incorporated herein by reference. A particularly suitable inflatable systems which allows the bulb or pump to be disconnected after inflation of the bladder is disclosed in the above identified U.S. Pat. No. 4,432,101.

As in the outer socket 20, the inner socket 40 is also molded to assume the configuration of the residual limb and also contains a similar inner cavity 42, lower section 44, pair of opposed ears 46 and interior surface 48. The inner socket 40 is adapted to conform to the inner surface contour 32 of bladder 30, and has preselected cut-out locations through its sidewall at 50, 52, 54 and 56. Cut-out locations 50, 52, 54 and 56 represent key contact bearing areas and when the composite socket is assembled, the bladder 30 serves to selectively apply pressure through the cut-out areas directly against the residual limb to control the movement and rotational stability of the prosthetic appliance. As illustrated more fully in FIGS. 1, 3 and 5, typical cut-out sections include posterior 50; medial 52; lateral 54; and proximal-medial 56, respectively. In some instances it may be possible for the composite socket Of the present invention to operate with a single cut-out section. The inner socket may be made of the same material described above for the outer socket.

The following example illustrates a method of making a composite socket of the present invention.

Example

The socket of the present invention is formed by conventional laminating techniques over a modified below-knee cast of a residual limb in the following manner: A plaster cast impression using a Plaster of Paris bandage available from Johnson & Johnson is first taken of the amputated extremity. After the cast has set the cast impression is then filled with liquid plaster of Paris available from U.S. Gypsum and allowed to harden. A metal mandrel in the form of a one inch pipe, which later functions to mate with a holding fixture is placed at the end of the cast impression opposite the end of the residual limb. The plaster bandage material is then stripped from the hardened plaster mold of the individual's amputated extremity. In working on the mold to allow for ease in handling, the mandrel is mounted on a fixture, usually over a ¾ inch diameter metal rod. The next step is to modify the plaster mold in such a way that allowances are made for the various weight-bearing and non-weight-bearing surfaces of the residual limb. These areas are to be determined by the prosthetist in the usual manner he or she is accustomed to as is conventional in the art. This procedure involves both the addition to and/or removal of plaster material from the mold depending on needs of a given patient. As a general proposition, the weight-bearing areas of a below-knee residual limb would be the non-boney areas.

Conversely, the boney areas of the residual limb are in general not weight-bearing areas. It should be noted however, that each amputee is unique and therefore the expertise of the prosthetist is required to determine the exact weight-bearing areas as opposed to the non-weight-bearing areas. After the cast has been properly modified by the prosthetist, the fabrication of the prosthetic socket is begun.

The fabrication procedure is as follows: The plaster mold of the residual limb is covered with a sheet of polyvinyl alcohol (pva) that is pulled into the cast by vacuum pressure. The PVA forms a bag that surrounds the entire mold and is sealed with tape at the mandrel end after a vacuum tube has been inserted into the PVA bag. The PVA is in the form of a roll 40 inches wide and has a thickness of 0.003 inches and is available from Durr-Fillauer of Chattanooga, Tenn. Prior to use, the PVA sheet is wetted with water to make it more pliable and easier to work with. In the present invention, the vacuum is drawn using a ¼ H. P. Dayton 2Z488 vacuum pump. This pva sheet acts as a parting agent and keeps the liquid resin from coming in contact with the plaster mold. Within the prosthetic industry a lamination may be defined as the introduction of liquid resin into various layers of materials under pressure. A commonly used lamination material is known as stockinette. The pressure created by the vacuum pump draws laminating resin into the stockinette material impregnating the material completely. The types of and numbers of layers of material as well as the kinds of material vary depending on the desires of the prosthetist and the needs of the amputee. Two types of liquid laminating resin are generally used-polyester and acrylic. Each has it own distinct advantages. The lay-up material for the sockets is generally nylon and/or fiberglass stockinette with pieces of fiberglass reinforcement. The stockinette material used in the present invention was nylon stockinette in 3 inch wide rolls from Durr-Fillauer. Other materials may be added to the lamination to increase the strength of the socket. These materials include carbon fiber, carbon fiber tape, dacron, cotton, rayon and others.

In the present invention, the common procedure for the lamination would be as follows: After the pva sheet is pulled over the plaster mold, eight to ten layers of nylon stockinette are pulled over the pva sheet. The number of layers of material (stockinette) determine how rigid and strong the socket becomes. In the case of the inner socket, it should be quite rigid. After the stockinette is applied, an outer pva bag is applied to cover the stockinette build-up. The PVA bag is open on both ends and 6 inches in diameter and 40 inches long having a wall thickness of 0.003 inches (Durr-Fillauer). In operation, the bag is first sealed at the mandrel end of the mold and the resin is then poured in the open end which surrounds the end of the residual limb. This end is then also sealed during the lamination process. Vacuum pressure is then applied to the interior of outer pva bag through a vacuum tube which has been inserted and sealed at the mandrel end. Approximately 500 ml of liquid resin has been poured into the outer pva bag and the vacuum pressure pulls the resin into the stockinette and impregnates all the layers of stockinette and other build-up materials. The inner pva sheet protects the plaster mold from coming in contact with liquid resin. In the present invention liquid polyester resin No. 4110 available from American Cyanimid was used. Another suitable resin called Acrylic Lamination Resin also from American Cyanimid can also be used.

After the liquid resin hardens another pva sheet is pulled over the now laminated inner socket. A bladder (these will be available in a variety of preformed sizes) is then placed over the pva sheet. The bladder itself typically is made out of rubber or vinyl. The prosthetist will select the one he/she feels is the best sized for their particular application. Next, another pva sheet is then placed over the bladder and a second laminated socket is then constructed in the same manner as the first or inner socket. This second socket may or may not have the same lay-up material as the inner socket. This depends on how strong the prosthetist wants the socket to be for a particular application. After the socket cures (becomes rigid) the plaster mold is removed from the laminated sockets.

The above procedure has resulted in the formation of an inner socket and outer socket with an inflatable bladder sandwiched in between. After the three pieces are separated the inner socket is examined by the prosthetist for the placements of the openings or cut-out areas, through the wall thickness. After the openings in the inner socket are created, the inner socket bladder and outer socket are reassembled. At this time, the bladder can be inflated. This inflation will cause migration of the bladder through the opening or openings in the inner socket and cause pressures to be exerted against the residual limb. The outer socket, which does not having any openings, will retain the bladder as well as the inner socket.

The material for the infaltable bladder can comprise any suitable material such as vinyl or robber. Once the selective openings have been formed in the sidewall of the inner socket, the, composite socket is reassembled and when the bladder is inflated due to pressure caused by bulb 38 through hose 39, the air bladder 30 will migrate through the inner socket opening or holes 50, 52, 54 and 56, respectively, to cause pressure over the common weight bearing areas of the stump in order to control the movement and rotational stability of the prosthetic device.

The exact size of the opening or openings of the internal socket referred to above will depend on the configuration of the residual limb, its fleshiness and its muscle structure with the exact weight bearing areas, as previously discussed, to be determined by the prosthetist. For example, because the boney areas of the stump, the tibia, fibula and medial and lateral condyles will not be opened in the inner socket, the bladder will not be allowed to infiltrate these areas. This is a key and critical aspect of the present invention because to a certain degree the contours of the residual limb are dependent on the various contours of the honey prominences of the residual limb. It is these contours that help control the movement and rotational stability of the below prosthetic device.

The molding and laminating procedures described above are conventional techniques well known to the art. Alternatively, vacuum forming using a sheet of heated plastic such as polypropylene may also be used to form the sockets.

The forgoing examples and methods have been described in the specification for the purpose of illustration and not limitation. It should be understood that other modifications and ramifications of the present invention will occur to those skilled in the art based upon this disclosure and are intended to be within the scope of this invention.

What is claimed is:

1. A composite socket member for use with a prosthetic appliance for a residual limb which comprises:
   (a) an outer socket which defines an inner cavity generally conforming to the outer surface of a residual limb;
   (b) an inner socket which defines an inner cavity which conforms to and in use is in substantial contact with the outer surface of the residual limb, with said inner socket conforming to the shape of said outer socket and when nested within the cavity of said outer socket defines an air space between the inner surface of said outer socket and the outer surface of said inner socket;
   (c) an inflatable bladder being disposed between the inner surface of said outer socket and the outer surface of said inner socket; and
   (d) said inner socket containing at least one opening through its side wall at a preselected weight-bearing location whereby upon inflation of said bladder, pressure is applied by said bladder through said wall opening against said preselected weight-bearing location of the residual limb to control the movement and rotational stability of the prosthetic appliance.

2. The member of claim 1 in which the inner socket contains a plurality of openings through its side wall at a plurality of preselected weight bearing locations.

3. The member of claim 1, in which the inflatable bladder contains independently controlled inflation means.

4. The member of claim 1 in which the inner and outer sockets are made of a molded plastic.

5. The member of claim 1 in which the sockets are made from a material selected from the group consisting of acrylic, polyester, carbon fiber, fiber glass and mixtures thereof.

6. A composite socket member for use with a prosthetic appliance for a residual limb which comprises:
   (a) an outer socket having an outer shell which defines an inner cavity generally conforming to the outer surface of a residual limb;
   (b) an inner socket which conforms to and in use is in substantial contact with the outer surface of the residual limb, and when nested in the cavity of said outer socket defines an air space between the inner surface of said outer socket and outer surface of said inner socket;
   (c) an inflatable bladder being disposed between the inner surface of said outer socket and the outer surface of said inner socket; the bladder containing independently controlled inflation means; and
   (d) said inner socket containing at least one opening through its side wall at a preselected weight-bearing location whereby upon inflation of said bladder, pressure is applied by said bladder through said side wall opening against said preselected weight-bearing location of the residual limb to control the movement and rotational stability of said prosthetic appliance.

7. A method of making a composite socket assembly for a prosthetic appliance for a residual limb which comprises:
   (a) forming a first plastic socket by coating a suitable molding material over a cast of a residual limb;
   (b) forming a stretchable air bladder over the outer surface of said first socket;
   (c) forming a second plastic socket by coating a suitable molding material over the outer surface of said bladder resulting in the formation of a composite socket assembly in the form of an inner plastic socket and an outer plastic socket having an air bladder sandwiched therebetween;
   (d) breaking the cast out of the lamination leaving an inner socket, air bladder and outer socket in place;
   (e) removing the inner socket from said assembly, and forming at least one preselected hole in the side walls of said inner socket in a preselected weight-bearing area or areas for the stump of said residual limb; and
   (f) reassembling said inner socket back to its original position resulting in the formation of a completed composite socket assembly having a uniform outer socket, an internal socket with at least one side wall hole at a selected pressure point or points, with an inflatable bladder disposed between the side walls of said outer and inner sockets.

* * * * *